United States Patent [19]

Kelly

[11] 4,329,309
[45] May 11, 1982

[54] PRODUCING RETICULATED THERMOPLASTIC RUBBER PRODUCTS

[75] Inventor: William G. F. Kelly, Middlesex, N.J.

[73] Assignee: Johnson & Johnson, New Brunswick, N.J.

[21] Appl. No.: 179,593

[22] Filed: Aug. 19, 1980

Related U.S. Application Data

[60] Continuation-in-part of Ser. No. 67,850, Aug. 20, 1979, abandoned, which is a continuation-in-part of Ser. No. 36,726, May 5, 1979, Pat. No. 4,305,990, which is a division of Ser. No. 848,439, Nov. 3, 1977, Pat. No. 4,173,612.

[51] Int. Cl.³ .............................................. B29D 7/14
[52] U.S. Cl. .................................. 264/167; 264/154; 264/171; 264/175; 264/210.2; 264/284; 428/134

[58] Field of Search ............... 264/167, 175, 156, 284, 264/171, 49, 154, 210.1–210.2; 428/134, 131, 137, 519; 260/33.6 AQ; 128/284, 287, 290 R

[56] References Cited

U.S. PATENT DOCUMENTS

| | | | |
|---|---|---|---|
| 3,085,292 | 4/1963 | Kindseth | 264/175 |
| 3,881,381 | 5/1975 | Kalwaites | 264/284 |
| 3,956,223 | 5/1976 | Chiang et al. | 260/33.6 AQ |
| 4,013,752 | 3/1977 | Kalwaites et al. | 264/167 |
| 4,062,995 | 12/1977 | Korpman | 264/154 |
| 4,076,669 | 2/1978 | Harper | 260/33.6 AQ |
| 4,136,699 | 1/1979 | Collins et al. | 128/290 R |
| 4,220,579 | 9/1980 | Rinehart | 260/33.6 AQ |

Primary Examiner—Jeffery R. Thurlow
Attorney, Agent, or Firm—Charles J. Metz

[57] ABSTRACT

Thermoplastic rubber containing minor amounts of olefin polymer is directly extrusion-formed into reticulated film.

9 Claims, 3 Drawing Figures

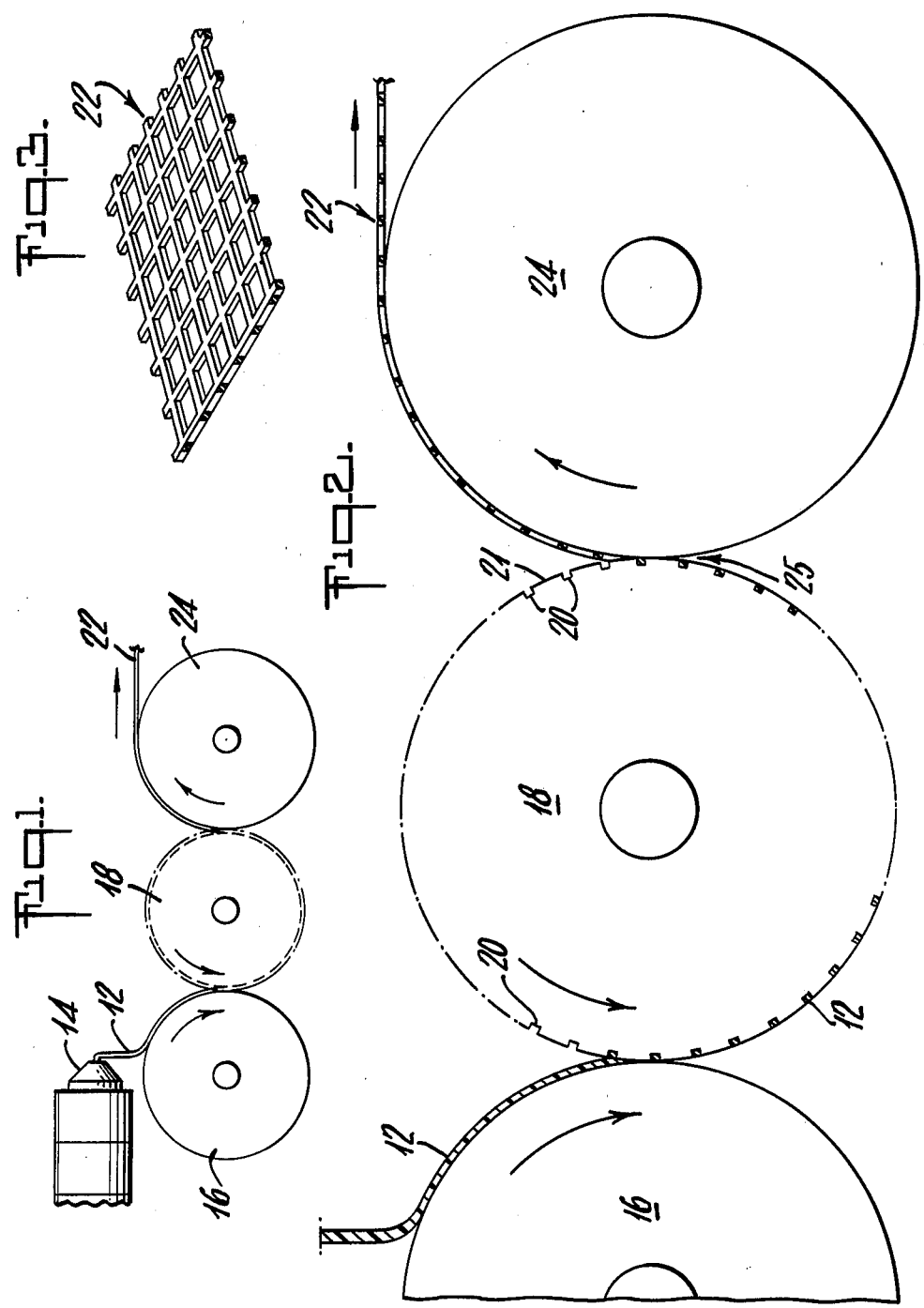

PRODUCING RETICULATED THERMOPLASTIC RUBBER PRODUCTS

This application is a continuation-in-part of application Ser. No. 67,850, filed Aug. 20, 1979 now abandoned, which is a continuation-in-part of application Ser. No. 36,726, U.S. Pat. No. 4,305,990 filed May 5, 1979, which is a division of application Ser. No. 848,439, filed Nov. 3, 1977, now U.S. Pat. No. 4,173,612.

The invention relates to a continuous process for forming reticulated film from thermoplastic rubber, and to the reticulated film produced therefrom, which has valuable utility as the elastic member in elasticized disposable diapers.

BACKGROUND OF THE INVENTION

Thermoplastic rubber is a relatively new type of polymeric composition that has become commercially available within the past decade or so. These polymers have the useful property of behaving like rubber at normal use temperatures, without the need for vulcanization. And because they are not vulcanized, they can be processed by many of the normal thermoplastic resin procedures at elevated temperatures.

One serious problem has been encountered, however, in attempts to extrude film from thermoplastic rubber. Either because of too low melt strength, or excessive notch sensitivity, or both, pure thermoplastic rubber does not draw well when extruded into thin films. The preferred way to extrude films from thermoplastic polymers is to draw the extruded web at a rate of speed faster than the rate at which the molten material is ejected from the die. This causes a reduction in thickness. Typically, this reduction in thickness will be as much as three-fold or even more.

I have found, however, that when one attempts to extrude a film from pure thermoplastic rubber, the web cannot be drawn down at all. In fact, in many cases the web must be drawn at a rate of speed slower than the extrusion rate, to thereby produce a film having a thickness or gauge greater than the die gap. This is undesirable because the throughput rate is slow, and because gauge variations are magnified. And further, I have not been very successful in producing any films at all of pure thermoplastic rubber at thicknesses much less than about 10 mils because of an excessive tendency of the extruded webs to tear.

In my said earlier applications, I disclosed the addition of amorphous polypropylene to thermoplastic rubber to improve the processability of said rubber such that it can readily be extruded into films, while still retaining the characteristic properties of rubber. In application Ser. No. 67,850, now abandoned I disclosed that thermoplastic rubber containing amorphous polypropylene can be directly extrusion formed into reticulated film in a continuous process which employs a pair of counter-rotating rolls, the first roll being a smooth roll and the second having a resilient surface engraved with a series of intersecting grooves.

It has now been discovered that, in addition to amorphous polypropylene, a number of other olefin polymers can be employed as additives to thermoplastic rubber in a continuous, direct extrusion process for the production of reticulated film having exceptionally valuable utility as the elastic member in elasticized disposable diapers.

SUMMARY OF THE INVENTION

A mixture of the thermoplastic rubber and olefin polymer is extruded as a molten sheet directly onto a smooth, heated roll. The smooth roll is in contact with a second roll to form a nip. The second roll is cooled and has a resilient surface that is engraved with a series of intersecting grooves. The second roll preferably has a slightly higher peripheral speed then the first roll. As the molten sheet passes through the nip between the two rolls, the molten sheet fills the said intersecting grooves and forms an open reticulated sheet, which is solidified on the second roll and then removed therefrom. The reticulated sheet produced thereby has exceptional utility as the elastic member in an elasticized disposable diaper.

THE PRIOR ART

It is known to add thermoplastic polymers in varying proportions to thermoplastic rubbers. It has been suggested to blend "polypropylene" (meaning isotactic or crystalline polypropylene), polystyrene, polyethylene, ethylene-vinyl acetate copolymer, and polyurethane with thermoplastic rubber.

Kindseth, in U.S. Pat. No. 3,085,292, describes a process for making open mesh sheeting by extruding thermoplastic resin into the nip of a pair of counterrotating rolls, at least one of which is engraved with a pattern of intersecting grooves.

Kalwaites, in U.S. Pat. No. 3,881,381, and Kalwaites et al., in U.S. Pat. Nos. 3,632,269, 3,666,609, and 4,013,752, disclose a process for forming reticulated film of isotactic polypropylene or other orientable thermoplastic polymer by embossing a film of such polymer at elevated temperature with a resilient embossing roll while simultaneously cooling and drafting the resulting reticulated film.

Harper, in U.S. Pat. No. 4,076,669, discloses blends of amorphous polypropylene in thermoplastic rubber.

Korpman, in U.S. Pat. No. 4,062,995, discloses the production of reticulated film from a blend of thermoplastic rubber and a tackifying resin.

BRIEF DESCRIPTION OF THE DRAWINGS

FIG. 1 is a schematic view in elevation of an arrangement of apparatus suitable for producing reticulated thermoplastic rubber sheet material;

FIG. 2 is an enlarged cross-sectional view of the embossing roll having a resilient surface that is used in the process for making reticulated thermoplastic rubber sheet material; and FIG. 3 is a view in perspective of the reticulated sheet material produced in accordance with the invention.

DETAILED DESCRIPTION OF THE INVENTION

The sheet material of the invention contains thermoplastic rubber and an olefin polymer. The thermoplastic rubbers contemplated for use in the invention are known materials. They are block copolymers having blocks of polybutadiene or polyisoprene, and blocks of polystyrene. A review article discussing these materials is "Structure And Properties Of Block Polymers And Multi-phase Polymer Systems: An Overview Of Present Status And Future Potential", by S. L. Aggarwal, *Polymer*, Vol. 17, November 1976, pages 938–956. Two representative types of thermoplastic rubbers are the linear block copolymers (A-B-A) having a mid-block of polybutadiene or polyisoprene and end-blocks of polystyrene, and the "star" or "radial" block copolymers having from 4 to 20 "arms" connected to a common center. Each arm is an A-B block copolymer, the inner portion being polybutadiene or polyisoprene, with the outer portion being polystyrene.

The typical thermoplastic rubber contains discrete polystyrene domains in a rubbery matrix. Apparently the polystyrene domains act in a manner analogous to conventional chemical crosslinks. The resulting rubber acts as though it has been vulcanized, even though no chemical crosslinks are present.

When the thermoplastic rubber is heated to about 200° F., the polystyrene domains begin to soften, and at temperatures of the order of 300° F. to 400° F., the thermoplastic rubbers can be melt processed by mechanical working in a manner analogous to conventional thermoplastic compositions. Upon cooling, the discrete polystyrene domains are reformed, and the material again exhibits rubbery elastomeric properties.

The material that is employed with the thermoplastic rubber is an olefin polymer. The olefin polymer does the following to the mixture of thermoplastic rubber plus olefin polymer:

(a) It permits a draw ratio of greater than 1, as evidenced by the ability to draw down extruded sheets of the mixture to a thickness less than the extruder die gap; and (b) It renders the melt sufficiently tack-free to permit continuous extrusion forming.

In addition to these processing characteristics, the reticulated film product exhibits the below-listed properties that make it especially useful as the elastic member in an elasticized disposable diaper:

(a) Good balance of elasticity, modulus, and creep resistance so that the diaper will be gathered sufficiently for the duration of normal use to ensure a good fit, but the force per unit area is relatively low so that there is less redness, irritation, and marks on the skin than when a solid, narrower ribbon of elastic is used to impart the same overall elastic strength; and (b) Anti-blocking properties prevent or significantly reduce sticking to the diaper's backing film and facing sheet, thereby resulting in a less stiff, more conformable product than would be obtained if the reticulated film of U.S. Pat. No. 4,062,995 (Korpman) were used (this advantage is obtained when the reticulated film is held in place in the diaper by an intermittent pattern of adhesive binder extending through the openings in the film from the backing film to the facing sheet).

The olefin polymers that are employed with the thermoplastic rubber to impart the foregoing properties include isotatic polypropylene, polyethylene, amorphous polypropylene, polybutylene, ethylene/vinyl acetate copolymer, ethylene/ethyl acrylate copolymer, ethylene/methyl acrylate copolymer, polystyrene, and the like.

Amorphous polypropylene is essentially atactic polypropylene having an isotactic content of not more than about 20 weight percent, and preferably not more than about 10 weight percent.

The olefin polymer is employed in an amount sufficient to improve the processability of the thermoplastic rubber when extruding thin films or sheets. Such improvement is evidenced by the ability to draw down extruded webs of the rubber/olefin polymer mixture to thereby produce sheets or films having thicknesses less than the die gap. Further, the pressure in the extruder and die is greatly reduced, which permits more economical operation. The exact minimum amount of olefin polymer which must be employed in which must be employed in order to obtain the advantages of the invention varies somewhat from case to case, but it is usually of the order of about 10 weight percent, based on weight of rubber plus olefin polymer, although the proportion may be as low as about 5 weight percent (on the same basis) in some cases. The upper limit of olefin polymer will also vary from case to case, depending on the nature of the ingredients. At proportions above about 35 weight percent (on the same basis), a significant reduction in the characteristic rubbery elastomeric properties of the product begins to occur. This may be acceptable in some cases, and not in others. Thus, the upper limit of olefin polymer would be that point at which the product still retains significant rubbery elastomeric characteristics.

Other conventional materials, employed in the usual amounts, can be employed in the mixture for their known purposes. Such materials include pigments, anti-blocking agents, stabilizers, anti-oxidants, ultraviolet stabilizers, bonding aid, and the like.

The reticulated film of the invention is preferably produced by extruding a thin film of a mixture of the olefin polymer and thermoplastic rubber directly onto a forming apparatus (described below). Conventional extrusion apparatus can be employed. Melt temperatures will usually be within the range of from about 275° to about 500° F., and preferably from about 325° to about 450° F. Because of the radically different melting points and melt viscosities of the two (or more) materials, thorough mixing is more difficult than the usual case of mixing two different thermoplastic polymers. In some cases it has been found that mixing is enhanced by cooling the extruding screw. Extruder screws that are specifically designed for effective mixing are available, and may be preferred for efficient commercial operation.

The extruded film is formed into a reticulated sheet material. A preferred way to do this is to form the reticulated sheet directly from the extruded film without collecting the film as an intermediate product.

This can be done by the process which is schematically illustrated in the drawings.

Referring to the drawings, a mixture of thermoplastic rubber and olefin polymer is extruded in the form of a thin sheet 12 of molten material through a conventional slot die 14. The still molten sheet 12 is collected on a heated rotating roll 16 having a smooth surface. The heated smooth roll 16 has a predetermined peripheral speed. The temperature of the heated smooth roll 16 is such that the sheet 12 is molten and formable when the sheet 12 reaches the nip 17 between the roll 16 and a second roll 18. The second (embossing) roll 18 is in contact with the smooth roll 16 at the said nip 17 between the two rolls. The embossing roll 18 is cooled, and has a resilient engraved surface. The engraving is in the form of continuous recessed areas 20 surrounding discontinuous raised areas 21. For instance, a preferred engraved pattern has a first series of grooves running circumferentially around the surface of the embossing roll 18, and a second series of grooves running perpendicular to and intersecting the first series of grooves. The said second series of grooves are parallel to the longitudinal axis of the embossing roll 18. They are shown in cross-section and exaggerated form as 20 in the drawings.

The sheet 12 transfers from the smooth roll 16 to the embossing roll 18 at the nip 17 between the two rolls. The embossing roll 18 is cooled so that the thermoplastic rubber solidifies while it is in contact therewith. The embossing roll 18 preferably is rotating at a slightly higher peripheral speed than the smooth roll 16. In some cases, the two rolls 16, 18 can rotate at the same speed, and in others, the embossing roll 18 can be slightly slower than the smooth roll 16. There is a wiping action at the nip 17 which forces substantially all of the molten sheet 12 into the grooves 20, as is shown in enlarged and exaggerated form in FIG. 2.

The sheet begins to solidify in the form of a netting or reticulated sheet 22 while it is in contact with the embossing roll 18. The netting will have the same structure or pattern as the engraved grooves on the roll 18. A typical reticulated sheet product 22 is illustrated in FIG. 3.

A convenient way to remove the reticulated sheet 22 from the embossing roll 18 is to remove it onto a take-off roll 24, which is also cooled. The take-off roll 24 forms a nip 25 with the embossing roll 18, and can be rotating at about the same peripheral speed, slightly slower, or slightly faster than the embossing roll 18.

The surface of the heated smooth roll 16 is kept at a temperature such that the extruded sheet 12 is molten when it reaches the nip 17, as is evidenced by the sheet being able to form into a reticulated sheet upon contact with the embossing roll 18. Exact surface temperatures will vary from case-to-case, depending on the nature and temperature of the extruded sheet, the peripheral speed of the roll, and similar factors, but will usually be of the order of about 175° F. to about 350° F., and preferably about 200° F. to about 250° F.

The surface temperature of the embossing roll should be cool enough to solidify the formed reticulated sheet so that it can be taken off the roll and handled. Typical surface temperatures of the embossing roll are from about 100° F. to about 190° F., and more usually 140° F. to 170° F.

The take-off roll can be cooled to facilitate removal of the reticulated sheet, and to complete the solidification of the reticulated sheet, where needed.

Throughput rates of from about 10 to about 60 feet per minute have been used successfully.

The embossing roll preferably has a slightly higher peripheral linear speed than the heated smooth roll. The speed differential is usually within the range of from 1 or 2 percent to about 15 to 20 percent greater, with about 3 to about 6 percent greater being more usual. The percentages are based upon the speed of the embossing roll. Similar speed differentials are employed when the embossing roll has a slightly lower peripheral linear speed than the heated roll.

In the Examples below, the following polymers were employed:

A. Thermoplastic Rubbers

"Solprene P414" was a 60/40 butadiene/styrene radial block copolymer, and "Solprene P418" was an 85/15 isoprene/styrene radial block copolymer. These materials are further characterized as follows:

|  | Solprene P414 | Solprene P418 |
|---|---|---|
| Molecular weight | 150,000 | 300,000 |
| Specific gravity | 0.95 | 0.92 |
| Melt flow, 5 kg @ 200° C. | 2.2 | 2.2 |
| Inherent viscosity | 0.80 | 1.16 |
| Solution viscosity, cps. | | |
| 20% wt in toluene | 230 | 900 |
| 25% wt in toluene | — | 2300 |

| Physical Properties Compression Molded 2 Minutes At 300° F. | | |
|---|---|---|
| 100% modulus, psi | 600 | 140 |
| Tensile at break, psi | 4000 | 1400 |
| Elongation, % | 750 | 1050 |
| Shore A Hardness | 90 | 34 |

B. Olefin Polymers

1. "AFAX" 900-C-P" is an amorphous polypropylene having the following properties:

|  | Typical Value, AFAX 900-C-P | Test Method |
|---|---|---|
| Viscosity, cps. | | |
| at 350° F. (177° C.) | 5500 | Brookfield Thermosel |
| at 375° F. (191° C.) | 4000 | Brookfield Thermosel |
| Needle penetrations, mm/10 | 16 | ASTM D 1321-65 |
| Ring-and-ball softening point, °F., (°C.) | 310(154) | ASTM D 2398-68 |
| Density, lbs/gal (kg/liter) | | |
| at 75° F. (24° C.) | 7.2(0.86) | |
| at 375° F. (191° C.) | 6.1(0.73) | |
| Normal Application temperature: °F. (°C.) | 350-375 (177-191) | |
| Flash Point, °F. (°C.) | 500(260) | ASTM D 92 |
| Ash content, ppm | 10 | Hercules P-67-3 |
| Glass Transition temperature, °F. (°C.) | −6(−21) | duPont 990 thermal analyzer |
| Heat of fusion, Btu/lb, (cal/gm) | 13.5(7.4) | duPont 990 thermal analyzer |
| Heat capacity, Btu/lb/°F. | 0.66 | Perkin-Elmer DSC-2 |

2. DQDE-1868 is an ethylene/vinyl acetate copolymer having about 17–18 percent vinyl acetate.

3. "Elvax" 460 is an ethylene/vinyl acetate copolymer having a Melt Index (by ASTM D 1238) of 2.2–2.8 and a vinyl acetate content of 17.5 to 18.5 weight percent.

4. "Petrothene" UE 630 is an ethylene/vinyl acetate copolymer having 17 weight percent vinyl acetate and a Melt Index of 0.5.

5. Shell polybutylene 0300 is a poly(butene-1) having a Melt Index of 4.0.

EXAMPLE 1

Reticulated sheet material was produced from the following formulation:

|  | Parts, by weight |
|---|---|
| Solprene P418 | 78.8 |
| AFAX 900-E-P | 10 |
| Ethylene/Vinyl Acetate Copolymer (DQDE=1868) | 10 |
| Kemamide E | 1 |
| Ionol (antioxidant) | 0.2 |

(1) A fatty acid amide used as an anti-blocking agent.

The arrangement of apparatus illustrated in FIG. 1 was used. The extruder was a 2½ inch Egan having an L:D ratio of 24:1. The die was stopped to give a 20 inch wide die. The die gap was 15 mils. The extruder conditions were the following:

|  |  |
|---|---|
| Zone 1 °F. | 300 |
| Zone 2 °F. | 350 |
| Zone 3 °F. | 360 |
| Zone 4 °F. | 410 |
| Adaptor °F. | 458 |
| Die 1 °F. | 450 |
| Die 2 °F. | 440 |
| Die 3 °F. | 440 |
| Melt temperature °F. (approx.) | 375 |
| Screw RPM | 30 |
| Barrell Pressure, psi | 2600–2700 |

The roll conditions were the following:

|  | Peripheral speed, feet per minute | Surface temperature, °F. |
|---|---|---|
| Heated smooth roll | 12 | 220 |
| Embossing roll | 12½ | 150–160 |
| Take-off roll | 12 | 35 |

The embossing roll had a surface made of silicone rubber, and an engraved pattern of grooves. The individual grooves had a cross-section that was approximately square, 19 mils on a side. There were 20 grooves per inch in the machine direction and 16 grooves per inch in the cross direction.

The pressure at the nip between the heated smooth roll and the embossing roll was about 40 pounds per linear inch, and the pressure at the nip between the embossing roll and the take-off roll was about 20 pounds per linear inch.

Typical reticulated sheets made in this manner have machine direction filaments with diameters of about 14.4 mils, cross direction filaments with diameters of about 19.8 mils, power pull[1] on the first cycle of 0.56 at 100% elongation, and power pull after the 10th cycle of 0.52 with a 10 percent elongation.

(1) "Power pull" is a test employed to evaluate the rubbery characteristics of the material tested. A 1-inch wide strip is tested in an Instron tester for tensile strength by stretching to 100% elongation at a rate of 20 inches/minute, and recording the 100% tensile strength. The film is then relaxed, and the test is repeated for a total of 10 cycles. The 100% elongation tensile strength is recorded after the 10th cycle. An ideal or perfect rubber would have no change in tensile strength after the 10th cycle.

The above-described netting makes an excellent leg reinforcement for elastic disposable diapers.

In the preceding example, the heated smooth roll had a diameter of 8 inches and a chromed steel surface, the take-off roll had the same diameter and the same surface, and the embossing roll had a diameter of 6 inches.

The pressure at the nip between the heated smooth roll and the embossing roll is enough to penetrate the thin sheet and form the sheet into an open reticulated structure of intersecting filaments corresponding to the pattern of grooves on the embossing roll. The exact pressure has not been found to be narrowly critical, and pressures of the order from about 10 to about 150 pounds per linear inch, and more preferably from about 20 to about 55 pounds per linear inch, have been found to be acceptable.

EXAMPLE 2

Reticulated sheet material was produced from the following formulation:

|  | Parts by weight |
|---|---|
| Solprene 418 | 66.9 |
| Solprene 414 | 20.0 |
| Elvax 460 or UE 630 | 8.0 |
| Shell Polybutylene 0300 | 4.0 |
| Kemamide E | 0.8 |
| Ionol (anti-oxidant) | 0.2 |
| Irganox 1010 (anti-oxidant) | 0.2 |

The arrangement of apparatus illustrated in FIG. 1 was used. The extruder was a 2-½ inch Welex having an L:D ratio of 30:1. The die was stopped to give an 18 inch wide die. The die gap was 15 mils.

The extruder conditions were the following:

|  |  |
|---|---|
| Zone 1, °F. | 301 |
| Zone 2, °F. | 353 |
| Zone 3, °F. | 381 |
| Zone 4, °F. | 398 |
| Zone 5, °F. | 398 |
| Melt, °F. | 404 |
| Adaptor, °F. | 438 |
| Die 1, °F. | 443 |
| Die 2, °F. | 452 |
| Front Pressure, psi | 2955 |
| Adaptor Pressure, psi | 1670 |
| Screw RPM | 25 |

The roll conditions were the following:

|  | Peripheral Speed, feet per minute | Surface Temp. °F. |
|---|---|---|
| Heated Smooth Roll | 16.5 | 243 |
| Embossing Roll | 18 | 153–158 |
| Take-off Roll | 18 | 71 |

The embossing roll pattern and the pressure conditions in the rolls were the same as those described above in Example 1.

The reticulated sheet material thus produced required a pull of 0.7±0.1 pounds to stretch a ¾-inch wide strip to 100 percent elongation. The sheet had a weight of 0.33 pounds per square yard. When a ¾-inch wide by 1 inch long specimen is stretched in an Instron tester to 100 percent elongation at a pull rate of 20 inches per minute, and then released, the instantaneous elongation set is less than 15 percent.

The elastic reticulated sheet material made in accordance with the invention is especially useful as the elastic member in an elastic disposable diaper. For this application, a number of potentially conflicting requirements must be balanced. For instance, reticulated sheet material having a relatively high percentage of open area is desirable for "strike-through" bonding of the elastic in the diaper. In strike-through bonding, several glue lines (e.g., 3 to 5) are laid down longitudinally on the backing film of the diaper, the elastic reticulated sheet material, in a stretched condition, is superimposed on top of the glue lines, and the facing sheet is then placed on top of the elastic. The backing sheet is thus bonded to the facing sheet through the elastic reticulated sheet material. In order to achieve a relatively fast line speed in the diaper-producing machine, the open area of the elastic reticulated sheet material should be at least about 40 percent.

In order to achieve the desired elastic strength, however, there must be a certain minimum total cross-sectional area of longitudinal filaments in the reticulated sheet material. It has been found that there should be sufficient longitudinal filaments of sufficient cross-sectional area to yield a tensile strength at 100 percent elongation of about 0.4 to about 1 pound for a ¾-inch wide strip.

Balancing these two requirements, the preferred elastic reticulated sheet material for the diaper application has an open area of from about 40 percent to about 75 percent.

The requirement for the cross filaments appear to be much less critical. Sufficient cross filaments to stabilize the reticulated sheet material during processing is all that is required.

The materials described in the Examples above illustrate preferred materials for the diaper application.

What is claimed is:

1. Process for producing reticulated thermoplastic rubber sheet material which comprises:
   (a) extruding a thin molten sheet consisting essentially of a mixture of
      (i) thermoplastic rubber comprising a block copolymer of styrene and butadiene or isoprene, and
      (ii) sufficient olefin polymer to improve the processability of said thermoplastic rubber, as evidenced by the ability to achieve a draw ratio of greater than 1 while extruding said mixture, said olefin polymer being selected from the group consisting of isotactic polypropylene, polyethylene, amorphous polypropylene, polybutylene, ethylene/vinyl acetate copolymer, ethylene/ethyl acrylate copolymer, ethylene/methyl acrylate copolymer, and polystyrene;
   (b) feeding the extruded molten sheet directly to the surface of a smooth surfaced first roll at a first position on said surface, wherein said first roll is rotating at a first peripheral linear speed, wherein said first roll is in contact with a second roll at a second position on said surface disposed from said first position to form a nip between said first and second rolls, the second roll havings its longitudinal axis essentially parallel to the longitudinal axis of the first roll, wherein said second roll is rotating in a direction opposite to said first roll at a second peripheral linear speed equal to, slightly greater, of slightly less than said first peripheral linear speed, and wherein said second roll has a resilient surface with a pattern of continuous recessed areas and discontinuous raised areas disposed over its surface;
   (c) passing said molten sheet from said first position to said second position, with the surface temperature of said first roll being such that said sheet is in a formable state when it arrives at said second position;
   (d) passing said sheet through the nip between said first and second rolls, wherein the pressure at said nip is sufficient to penetrate said sheet and form said sheet into an open reticulated sheet of intersecting filaments corresponding in structure to said pattern of recessed areas on the surface of said second roll;
   (e) passing said open reticulated sheet around the surface of said second roll to a third position on the surface of said second roll disposed from said nip, wherein the surface of said second roll is maintained at a temperature such that said reticulated sheet is a solid, self-supporting structure when it arrives at said third position; and
   (f) removing said reticulated sheet from said second roll at said third position.

2. The process of claim 1 wherein said second peripheral linear speed is slightly greater than said first peripheral linear speed.

3. The process of claim 1 wherein said thermoplastic rubber is a radial block copolymer of styrene with isoprene or butadiene.

4. The process of claim 1 wherein the olefin polymer is employed in an amount within the range of from about 5 to about 35 weight percent, based on weight of thermoplastic rubber plus olefin polymer.

5. The process of claim 1, 2, 3, or 4 wherein the reticulated sheet is removed from second roll by feeding said reticulated sheet onto the surface of a third roll that is rotating in a direction opposite to said second roll at a third peripheral linear speed about equal to, slightly greater, or slightly less than, said second peripheral linear speed, the third roll having its longitudinal axis essentially parallel to the longitudinal axis of said second roll.

6. The process of claim 5 wherein said third roll is in contact with said second roll at said third position to form a nip between said second and third rolls.

7. The process of claim 1 or 2 wherein the olefin polymer is amorphous polypropylene.

8. The process of claim 1 or 2 wherein the olefin polymer is polybutylene.

9. The process of claim 1 or 2 wherein the olefin polymer is ethylene-vinyl acetate copolymer.

* * * * *